United States Patent [19]

Ikehara

[11] Patent Number: 5,232,365
[45] Date of Patent: Aug. 3, 1993

[54] PROCESS FOR PRODUCING DENTAL WORKING CAST

[75] Inventor: Isamu Ikehara, 21-18, Hantagawa 4-Chome, Naha-shi, Okinawa-ken 902, Japan

[73] Assignee: Isamu Ikekara, Japan

[21] Appl. No.: 837,753

[22] Filed: Feb. 18, 1992

[30] Foreign Application Priority Data

Feb. 20, 1991 [JP] Japan .................................. 3-045621

[51] Int. Cl.$^5$ ............................................. A61C 11/00
[52] U.S. Cl. ...................................... 433/213; 433/36; 433/74; 433/223; 264/19
[58] Field of Search ................. 433/213, 34, 36, 74, 433/223; 264/19, 16

[56] References Cited

U.S. PATENT DOCUMENTS

| | | | |
|---|---|---|---|
| 1,335,372 | 3/1920 | Fredericks | 264/19 |
| 2,409,783 | 10/1946 | Moskey | 433/223 |
| 3,647,488 | 3/1972 | Brighan et al. | 264/16 |
| 4,172,867 | 10/1979 | Devault | 264/16 |
| 4,238,189 | 12/1980 | Tirino | 433/74 |
| 4,253,835 | 3/1981 | Ware | 264/16 |
| 4,744,753 | 5/1988 | Ross | 264/16 |

Primary Examiner—John J. Wilson
Attorney, Agent, or Firm—McGlew and Tuttle

[57] ABSTRACT

The present invention relates to a process for producing dental working cast for use for preparing a crown or a denture of metal-bonded porcelein or of all ceramic in dental therapy, by preparing a removable positive model of tooth from impression, processing it into a model of the working cast and replicating the model using a suitable material chosen from resin, die material, refractory cast material and modified dental stone, to obtain the working cast.

3 Claims, 3 Drawing Sheets

PROCESS FOR PRODUCING DENTAL WORKING CAST

FIELD OF THE INVENTION

The present invention relates to a process for producing a dental working cast for use for preparing a crown or a denture of metal-bonded porcelein or of all ceramic for dental therapy purposes. The process involves the preparation of a removable positive model of a tooth from an impression, processing it into a model of the working cast and replicating the model using a suitable material chosen from resin, die material, refractory cast material and modified dental stone, to obtain the working cast.

BACKGROUND OF THE INVENTION

Heretofore, it has been the practice to produce a dentition model for producing a crown or bridge for dental therapy purposes, by replicating the objective tooth by taking an impression of the dentition including the ambient area around the objective tooth, followed by plaster molding. The so-prepared model of the die is then processed in a dental laboratory by a dental technician to settle reference planes by trimming the tooth end and each face with a trimmer, whereupon a dowel pin is placed on the bottom face of the reference plane by a dowel pin drill or dowel pin setter and is fixed with an adhesive or plaster. Then, a groove is formed on the outer or inner face of the dowel pin for preventing rotation thereof. The groove is formed by cutting with a point, whereupon this is coated with a release compound. The resulting removable die model is embedded in a mass of secondary pour plaster filled in a rubber case, in such a manner, that the upper part of the model above the row of dowel pins sinks beneath the upper face of the plaster. After the plaster has hardened, the plaster block is taken out of the rubber case and is cut off to leave the portion of the objective die. Then, the model of the objective die is separated from the cut portion by withdrawing it therefrom. The die of the abutment tooth is worked up by trimming into a finished shape permitting easy fit of a crown, bridge or the like. The so-trimmed die is then placed in the proper position on the tray of secondary pour plaster and is used for preparing the corresponding crown or bridge by adjusting the relative posture to the neighboring tooth dies and adjusting the engagement with the opposing tooth to be engaged therewith.

Also for producing an all ceramic denture, the model entire act of teeth is first prepared using a silicone rubber impression material and replicating with a refractory material therefrom to produce renewedly the working cast. Here, the expensive heat resistant dowel pins used in these work procedures have to be handed over to the dental surgeon without removing them.

As explained above, the prior art technique requires the cost of the entire die of teeth for preparing the objective abattment tooth, so that a large amount of expensive material has to be employed for the preparation. Such material cost is especially high for all ceramic dentures using silicone impression material and refractory cast material. In addition, the prior art operates to finish the crude die model by trimming, whereby its original contour is altered, which makes it difficult to recognize the actual position of ginvals around the reference planes of the die and the transition areas therebetween, when the unprocessed denture to be prepared, such as, a crown or the like, is placed on the working model for the adjustment work thereof.

SUMMARY OF THE INVENTION

The object of the present invention is, in general, to provide a process for producing dental working casts for use for preparing a crown or a denture of metal-bonded porcelein or of all ceramic for dental therapy purposes, by separately replicating only the die to be processed without necessitating total replication of the entire die model and, thus, without any damage of the die model, to form the die of the corresponding abutment tooth.

For attaining the above object, the present invention seeks to prepare a model of a working cast by separating only the portion of the abutment tooth from the plaster dentition model taken by the dentist and the so-separated die of the abutment tooth is employed for producing the working cast and, for producing an all ceramic denture, an unexpensive dowel pin of a refractory material is employed.

BRIEF DESCRIPTION OF THE INVENTION

FIG. 1 illustrates a perspective view of a dentition model.

FIGS. 2(A) and 2(B) illustrate each a schematic vertical sectional view of an embodiment of the lower impression tray according to the present invention with a different embedded model of an abutment tooth, FIG. 3 shows schematically the upper and the lower tray corresponding to FIG. 2(A) in the combined position in a vertical section.

FIG. 4 shows schematically the upper and the lower tray of another embodiment according to the present invention having a charging inlet for the molding material.

DETAILED DESCRIPTION OF THE INVENTION WITH PREFERRED EMBODIMENTS

Below the invention is described in detail with reference to the appended Drawings by way of Examples.

Figure 1:
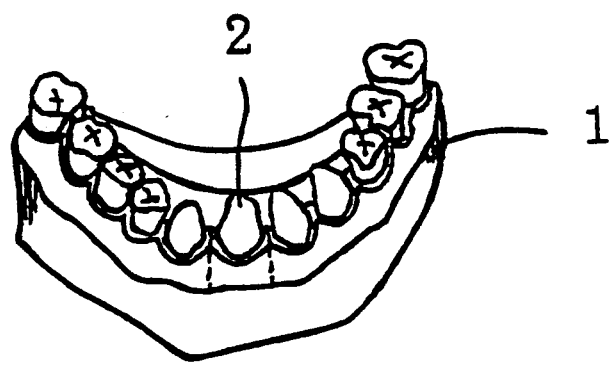

A plaster dentition model 1 taken by a dentist is cut along the dotted line indicated in FIG. 1 to separate the die 2 of the abutment tooth to be treated.

Figure 2A:
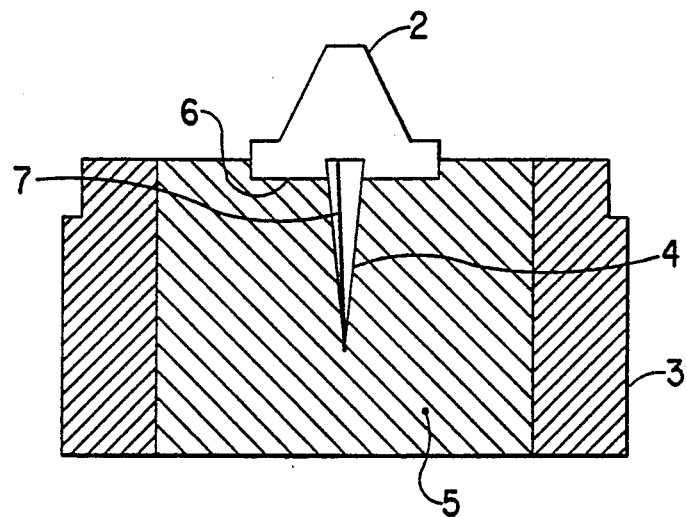
Figure 3:
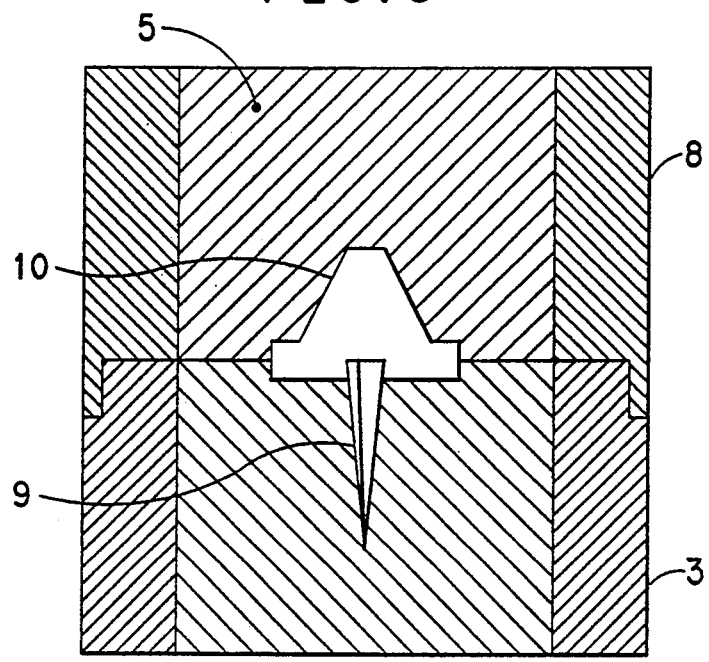

On a lower impression tray 3 according to the present invention filled with an impression material 5, as shown in FIG. 2(A), the so-separated die 2 is placed for replicating the lower portion thereof including the reference plane 6 and a dowel pin 4. The dowel pin 4 is provided with a rotation preventing groove 7 on its side face. Onto the lower tay 1 tray 3 prepared as above, i.e. having partly embedded the die 2 of the abutment tooth, there is then fitted an upper tray 8 according to the present invention. This upper tray 8 is coupled with the lower tray 1, as shown in FIG. 3, whereupon the vacant cavity inside the upper tray 8 is filled with the impression material 5 by pouring it via an adequate charge inlet. After hardening of the charged impression material, the upper and the lower trays (3.8) are separated with each other and the hardened impression material is cut apart along the upper face of the lower tray 3 and the die 2 of the abutment tooth with the dowel pin 4 is withdrawn from the separated impression material. Then, a separately prepared dowel pin 9 having the same size and contour as the dowel pin 4 and made of an unexpensive refractory material is inserted in the resulting cavity in the lower half of the hardened impression, whereupon this is put together with the upper half of the hardened impression to form the casting mold and the remaining vacant cavity of the thus formed mold is filled with a cast material 10 of a refractory or resin, in order to obtain, after hardening of the cast material 10, the corresponding working cast.

It is preferable to furnish the interface between the upper and the lower hardened impressions of the mold with, for example, (1) a suitable pin inserted through the wall of the mold, (2) a special fitting contour for fitting engagement or (3) an insertable engagement means by bolt and receptacle, for simple and reliable positioning of them relative to each other.

Figure 2B:
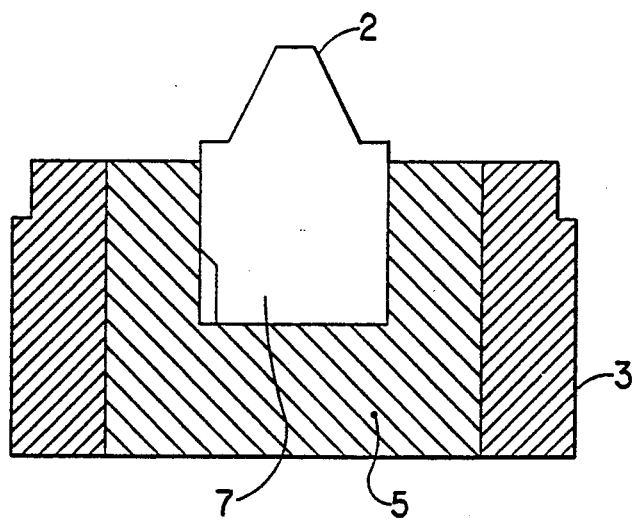

In the case of working with the die of the abutment tooth provided in itself with a rotation preventing means and, thus, without combined with dowel pin, the primary molding with an impression material is more simplified, wherein it is required only to place the separated die of the abutment tooth in the mass of the impression material as shown in FIG. 2(B).

Figure 4:
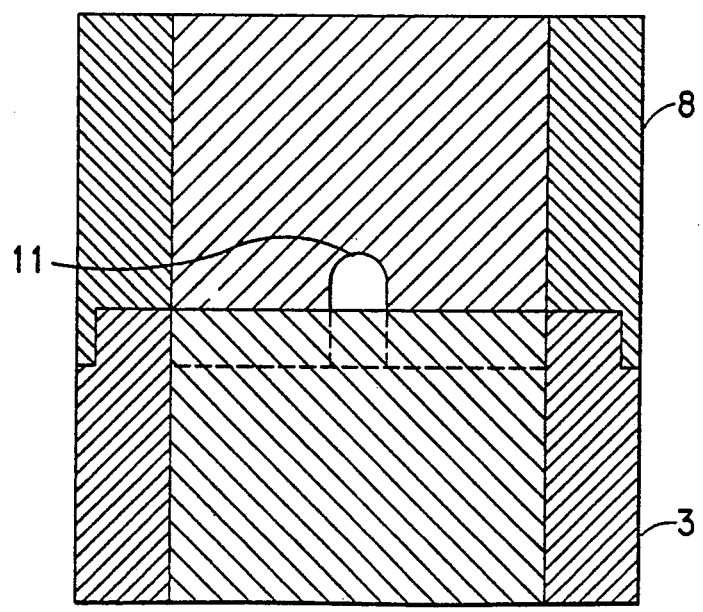

It is preferable to provide an inlet opening 11 at about the combination zone (interface) between the upper and lower trays as shown in FIG. 4, in order to facilitate replenishing of the primary molding material (namely, an impression material) after the two trays have been put together, to thereby prevent eventual displacement of the reference plans due to interference by the molding material included at the combination part between the upper and lower trays.

As described above, it is permitted according to the present invention to economize the expenditure from the molding materials for producing a working cast of an abutment tooth, since only the abutment tooth to be treated is reproduced by the molding without necessitating to realize an inclusive replication.

Since the die model supplied from the dentist is not subjected to any alteration by, such as trimming etc., except the cutting gout of the die of the abutment tooth to be worked, the adjustment work of the denture, such as crown or bridge, can be effected accurately by returning the die to the model. It is advantageous also that a complete reproduction of the working cast can easily be realized when it has suffered damage by accident etc. It is furthermore advantageous that inexpensive dowel pins can be employed for working an all ceramic denture.

I claim:

1. A process for producing a dental working cast for use for preparing a crown or denture of metal-bonded porcelein or of all ceramic in dental prosthetic treatment, comprising cutting and separating from the plaster dentition model taken by a dentist the portion of the die of the abutment tooth to be processed, processing the so-separated die of the abutment tooth so as to provide it with a rotation preventing means, placing in a mass of an impression material, which is filled in a lower tray capable of being combined fittingly and position-definitely with an upper tray to form a casting mold, said separated and processed die of the abutment tooth, combining the thus prepared lower tray having the impression material and the die of the abutment tooth together with the upper tray to form the casting mold, charging the vacant inside space of the thus formed mold with the impression material to fill up the mold, permitting the impression material to harden, separating the upper and the lower trays with each other, parting the hardened impression material along about the upper face of the lower tray, withdrawing the die of the abutment tooth from the parted halves of the impression, putting this lower half of the impression together with the upper half of the impression having a vacant cavity corresponding to the die of the abutment tooth in a position-definite relationship with each other, charging the vacant cavity with a cast material of a refractory, or a resin and permitting the so-charged cast material to harden to form the working cast.

2. A process for producing a dental working cast for use for preparing a crown or denture of metal-bonded porcelein or of all ceramic in dental prosthetic treatment, comprising cutting and separating from the plaster dentition model taken by a dentist the portion of the die of the abutment tooth to be processed, placing in a mass of an impression material, which is filled in a lower tray capable of being combined fittingly and position-definitely with an upper tray to form a casting mold, a dowel pin provided with a rotation preventing means and, on this dowel pin, said separated die of the abutment tooth, combining the thus prepared lower tray having the impression material, dowel pin and the die of the abutment tooth together with the upper tray to form the casting mold, charging the vacant inside space of the thus formed mold with the impression material to fill up the mold, permitting the impression material to harden, separating the upper and the lower trays with each other, parting the hardened impression material along about the upper face of the lower tray, withdrawing the die of the abutment tooth and the dowel pin from the parted halves of the impression, inserting a new dowel pin made of a refractory material and having the same size and contour as the previous dowel pin withdrawn, putting this lower half of the impression having inserted said new pin together with the upper half of the impression having a vacant cavity corresponding to the die of the abutment tooth in a position-definite relationship with each other, charging the vacant cavity with a cast material of a refractory or a resin and permitting the so-charged cast material to harden to form the working cast.

3. Process according to claim 1 or 2, wherein an inlet opening for charging the impression material into the vacant inside space of the mold formed from the upper and lower trays is located at about the combination zone of the upper and lower trays and wherein the lower tray is filled, before putting together with the upper tray, with insufficient amount of the impression material and, after the two trays have been put together, the vacant inside space is filled by supplementing the impression material via said inlet opening.

* * * * *